(12) United States Patent
Salour

(10) Patent No.: US 8,201,997 B1
(45) Date of Patent: Jun. 19, 2012

(54) IMAGING TEMPERATURE SENSING SYSTEM

(75) Inventor: Michael M. Salour, Carlsbad, CA (US)

(73) Assignee: IPITEK, Inc., Carlsbad, CA (US)

( * ) Notice: Subject to any disclaimer, the term of this patent is extended or adjusted under 35 U.S.C. 154(b) by 589 days.

(21) Appl. No.: 12/475,044

(22) Filed: May 29, 2009

Related U.S. Application Data

(60) Provisional application No. 61/056,872, filed on May 29, 2008.

(51) Int. Cl.
  *G01J 5/08* (2006.01)
  *A61B 6/08* (2006.01)
  *A61B 1/05* (2006.01)
  *A61B 1/005* (2006.01)

(52) U.S. Cl. .......... 374/131; 374/161; 374/137; 356/43; 600/101; 600/474

(58) Field of Classification Search .......... 374/100, 374/131, 132, 120, 137, 161; 356/43; 600/473, 600/474, 478, 101
See application file for complete search history.

(56) References Cited

U.S. PATENT DOCUMENTS

| 4,448,547 A * | 5/1984 | Wickersheim | 374/131 |
| 4,621,929 A * | 11/1986 | Phillips | 374/43 |
| 4,689,483 A * | 8/1987 | Weinberger | 250/227.23 |
| 4,703,175 A * | 10/1987 | Salour et al. | 356/45 |
| 4,979,133 A * | 12/1990 | Arima et al. | 702/134 |
| 5,004,913 A * | 4/1991 | Kleinerman | 250/227.21 |
| 5,051,595 A * | 9/1991 | Kern et al. | 250/458.1 |
| 5,258,602 A * | 11/1993 | Naselli et al. | 219/497 |
| 5,304,809 A * | 4/1994 | Wickersheim | 250/458.1 |
| 5,348,396 A * | 9/1994 | O'Rourke et al. | 374/161 |
| 6,330,479 B1 | 12/2001 | Stauffer | |
| 6,564,088 B1 * | 5/2003 | Soller et al. | 600/478 |
| 6,975,899 B2 * | 12/2005 | Faupel et al. | 600/476 |
| 7,416,330 B2 * | 8/2008 | Ito et al. | 374/127 |
| 2004/0064053 A1 * | 4/2004 | Chang et al. | 600/478 |
| 2005/0251235 A1 | 11/2005 | Schlorff et al. | |
| 2008/0097225 A1 * | 4/2008 | Tearney et al. | 600/478 |
| 2009/0059996 A1 * | 3/2009 | Komeda et al. | 374/161 |

OTHER PUBLICATIONS

T. Juang et al., Construction of a Conformal Water Bolus Vest Applicator for Hyperthermia Treatment of Superficial Skin Cancer, Internat. Con. of the IEEE Eng. in Med. and Bio. Soc., Sep. 2004, pp. 1-4, San Francisco.

T. V. Samulski et al., Clinical Experience with a Multi-element Ultrasonic Hyperthermia System: Analysis of Treatment Temperatures, Internat. J. Hyperthermia, Sep. 1990, pp. 909-922, vol. 6, No. 5.

C. J. Diederich et al., Preclinical Evaluation of a Microwave Planar Array Applicator for Superficial Hyperthermia, Internat. J. Hyperthermia, Mar. 1993, pp. 227-246, vol. 9, No. 2.

C. J. Diederich et al., An Improved Bolus Configuration for Commercial Multielement Ultrasound and Microwave Hyperthermia Systems, Med. Phys., Jun. 1994, pp. 1401-1403, vol. 21, No. 9.

P. R. Stauffer et al., Preliminary Clinical Experience with Planar and Conformal Microwave Array Applicators for Hypothermia, Abstract of presentation given at 14th North American Hyperthermia Society Meeting, 1994, Nashville TN.

(Continued)

*Primary Examiner* — Gail Verbitsky
(74) *Attorney, Agent, or Firm* — Burns & Levison LLP; Jacob N. Erlich

(57) ABSTRACT

An imaging temperature sensing system having at least one imaging component and at least one temperature sensing component, thus providing means for implementing temperature sensing and imaging within a single device.

9 Claims, 4 Drawing Sheets

OTHER PUBLICATIONS

P. R. Stauffer, Thermal Therapy Techniques for Skin and Superficial Tissue Disease, Critical Review: Matching the Energy Source to the Clinical Need, SPIE Optical Engineering Press, 2000, pp. 327-367.

P. R. Stauffer et al., Progress on System for Applying Simultaneous Heat and Brachytherapy to Large-area Surface Disease, Proc. of SPIE, 2005, pp. 82-96, vol. 5698.

T. Juang et al., Multilayer Conformal Applicator for Microwave Heating and Brachytherapy Treatment of Superficial Tissue Disease, Int. J. Hyperthermia, Nov. 2006, pp. 527-544.

P. R. Stauffer, Progress on Conformal Microwave Array Applicators for Heating Chestwall Disease, Proc. of SPIE, 2007, pp. 1-13, vol. 6440.

K. Arunachalam et al., Performance Evaluation of a Conformal Thermal Monitoring Sheet Sensor Array for Measurement of Surface Temperature Distributions During Superficial Hyperthermia Treatments, Int. J. Hyperthermia, 2008, pp. 313-325, vol. 24, No. 4.

K. Arunachalam et al., A Thermal Monitoring Sheet With Low Influence From Adjacent Waterbolus for Tissue Surface Thermometry During Clinical Hyperthermia, IEEE Trans. Biomed. Engr., Oct. 2008, pp. 2397-2406, vol. 55, No. 10.

P. R. Stauffer, Devices and Techniques for Thermal Therapy of Chest Wall Recurrence, Abstract of presentation for Society for Thermal Medicine 2006 Annual Meeting, 2006, Bethesda MD.

T. Juang et al., Improved Patient Interface for a Multilayer Conformal Applicator for Simultaneous Heat and Brachytherapy Treatment of Superficial Tissue Disease, Abstract of presentation for Society for Thermal Medicine 2006 Annual Meeting, 2006, Bethesda MD.

P. Stauffer et al., Progress on Conformal Microwave Array Applicators for Heating Large Area Chest Wall Disease, Abstract of presentation for Euro. Soc. for Hyperthermic Oncology 24th Annual Meeting, Jun. 2007, Prague.

K. Arunachalam et al, Characterization of Surface Thermometry Approaches for Clinical Hyperthermia, Abstract of presentation for 10th Int. Congress on Hyperthermic Oncology, Apr. 2008, Munich.

Paul R. Stauffer et al., U.S. Appl. No. 12/475,151, filed May 29, 2009, titled Thermal Monitoring Device.

Celestino J. Gaeta, U.S. Appl. No. 12/429,463, filed Apr. 24, 2009, titled Passive Wavelength-Division Multiplexing (WDM) Fiber-Optic Temperature Sensor.

Michael M. Salour, U.S. Appl. No. 12/468,598, filed May 19, 2009, titled Multiple Sensing Tip Optical Fiber Thermometer.

* cited by examiner

IMAGING TEMPERATURE SENSING SYSTEM

CROSS REFERENCE TO RELATED APPLICATIONS

This application claims priority of provisional application Ser. No. 61/056,872 filed May 29, 2008 entitled OPTICAL FIBER THERMOMETER WITH IMAGING and which provisional application is incorporated herein in its entirety.

BACKGROUND

Various embodiments of this invention relate generally to endoscopic medical examination or surgery, as well as temperature sensing or mapping in medical applications.

Past endoscopic medical procedures involve a flexible conduit capable of relaying images that is inserted into a patient's body. Other tools may also be inserted to measure parameters such as temperature or to perform surgery. Specifically, fiber-optic temperature sensors employed for medical applications are typically inserted into a patient and guided to a particular location using an x-ray or other imaging system, thus providing a limited two-dimensional view. Alternatively, an endoscope may be used to aid in directing and positioning a sensing tip of a fiber optic thermometer within a patient's body. However, this process involves two separate components so that the endoscope may have to be re-positioned and re-oriented when the fiber is moved. It also involves having to manipulate at least two different instruments (endoscope and fiber thermometer).

It is therefore a need to develop a single endoscope-like instrument capable of imaging and temperature measurement within a patient's body.

SUMMARY

The needs for the invention set forth above as well as further and other needs and advantages of the present invention are achieved by the embodiments of the invention described herein below.

Various embodiments of this invention allow the addition of a view-port at the sensing element of a fiber-optic thermometer, which allows for more precise location of a sensing tip of the fiber-optic thermometer. Furthermore, it also allows for a visual inspection of the area within a body where the temperature is to be monitored, which can be an additional diagnostic during medical treatments including, but not limited to, microwave treatment for certain types of cancer.

Features of a fiber-optic endoscope and a fiber-optic thermometer may be incorporated in a single, compact device. Two principle technologies are involved. One technology is the temperature-dependent fluorescent-decay of an atomic resonance. Measurements are based upon the temperature-dependent fluorescence-decay process of a phosphor bonded to the end of an optical fiber, which constitutes the temperature probe.

The other technology is fiber-optic imaging. Multiple fibers may be arranged to form a composite optical fiber with an effectively larger diameter. The cross-section of an individual fiber may be on the order of a few microns in diameter, with an inner core of slightly higher optical index of refraction relative to the surrounding cladding layer. In contrast, the overall diameter of the composite fiber bundle may typically be on the order of a few hundred microns. A lens may be used to image an object onto one end of the fiber bundle. The light from the object that enters a given individual fiber will be transmitted to the opposite end of the bundle by total internal reflection of light rays within that individual fiber (alternatively, the light propagates within the optical fiber waveguide structure). If the relative arrangement of the fibers within the cross-section of the fiber bundle is maintained along its length, then the image of the object is transmitted to the other end of the bundle in a pixel format.

For a better understanding of the present invention, together with other and further needs thereof, reference is made to the accompanying drawings and detailed description and its scope will be pointed out in the appended claims

DETAILED DESCRIPTION

Figure 1:
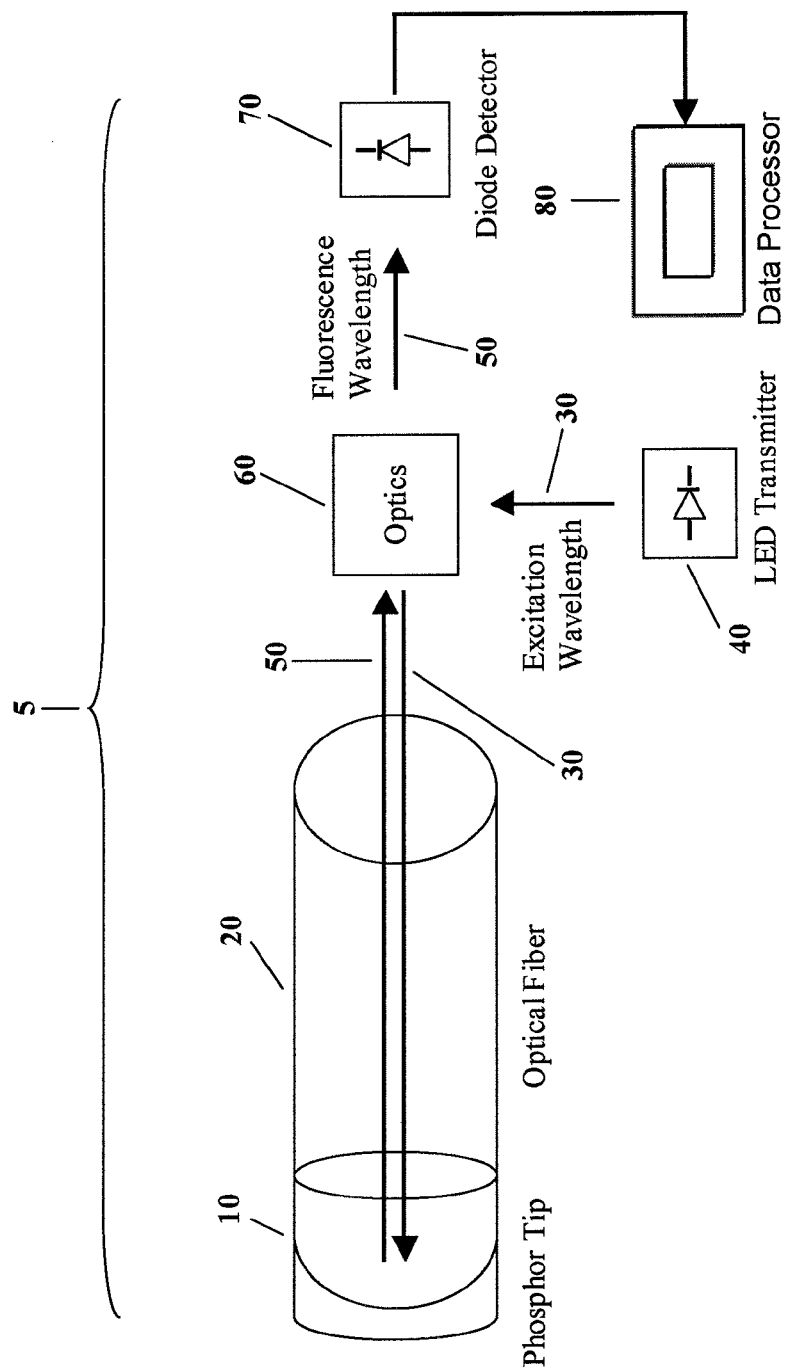
FIG. 1 is a schematic block diagram illustration of a temperature-dependent fluorescence-decay temperature sensor.

Various embodiments of this invention allow for substantially simultaneous measurement of temperature of a surface and visual observation of the surface via optical fibers. A fiber-optic temperature sensor may utilize, for example, but not be limited to, temperature-dependent fluorescence-decay of an atomic resonance to measure temperature. In the example shown in FIG. 1, temperature sensor 5 includes a temperature-sensing component 10 in the form of, but not limited to, a phosphor, which exhibits temperature-dependent fluorescence-decay. The temperature-sensing component 10 is attached, for example, by, but not limited to, gluing, to substantially the end of an optical fiber 20. In this embodiment, excitation electromagnetic radiation 30 such as, but not limited to, light in the form of optical pulses from a device such as, but not limited to, a low-power, broadband light-emitting diode (LED) source 40 propagates along the fiber 20 to the phosphor material or temperature-sensing component 10. The phosphor absorbs the optical energy from the optical pulses 30 at the excitation wavelength and spontaneously emits fluorescence emission light 50 at a fluorescence wavelength. A portion of the fluorescence emission light 50 is captured by the optical fiber 20 and propagates in the optical fiber 20 back toward optics 60 such as, but not limited to, beamsplitters, gratings, or waveguide directional couplers, where it is separated from the path of the excitation electromagnetic radiation 30 by the optics 60 and directed to detector, such as, but not limited to, an optical detector 70.

While the excitation electromagnetic radiation (light pulse) 30 is present at the temperature-sensing component (phosphor) 10, the fluorescence emission light 50 slowly increases toward a maximum value. After the excitation electromagnetic radiation (light pulse) 30 is switched off, the fluorescence emission light 50 then begins to decay (decrease in power of signal). A higher temperature typically yields a faster decay process. A conventional calibration procedure is used in, but not limited to, a data processor 80 to correlate the temporal decay process with temperature of the temperature-sensing component (phosphor) 10.

Figure 2:
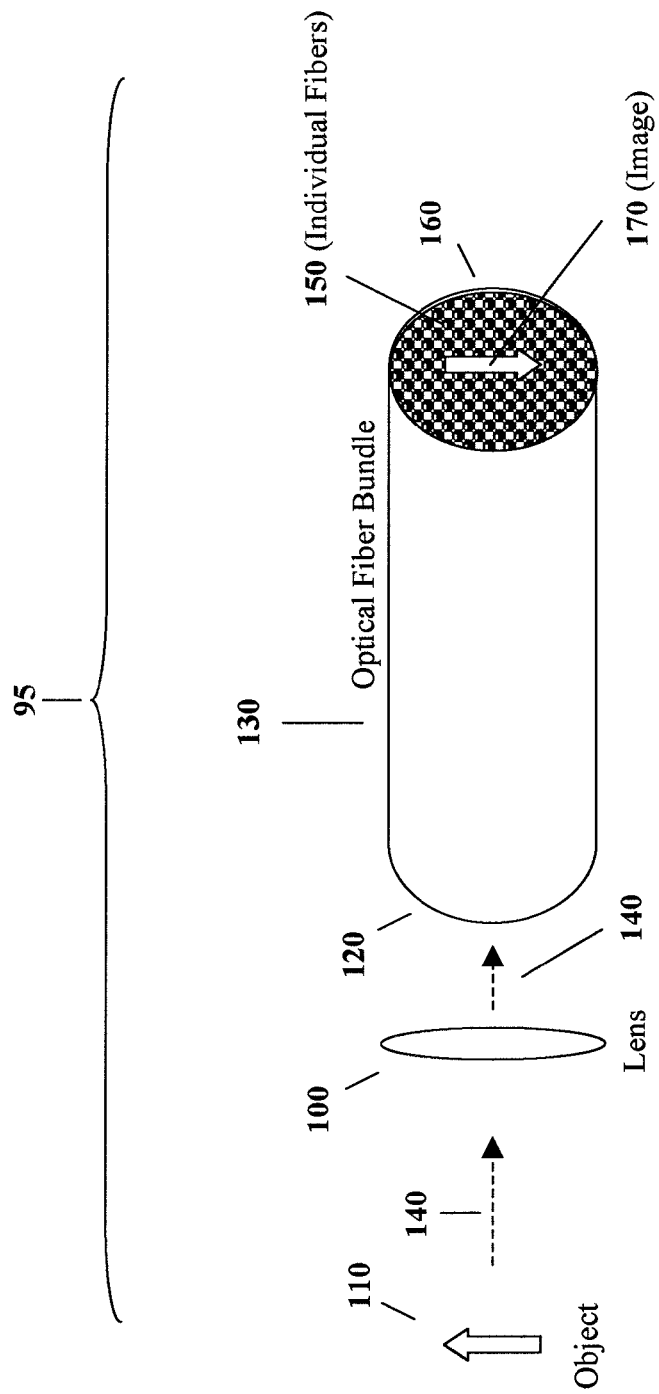
FIG. 2 is a schematic block diagram illustration of an optical fiber bundle for imaging.

An example, not limiting the present embodiments, is a system for imaging with fiber optics is presented schematically in FIG. 2. An imaging system 95 may employ a lens 100, which is used to image an object 110 via a fiber bundle 130. Light 140 from the object 110 propagates through the lens and onto a first endface 120 of the fiber bundle 130 where a portion of the light 140 enters individual fibers 150 comprising the fiber bundle 130, and subsequently propagates to a second endface 160 of the fiber bundle 130, forming an image 170 of the object 110.

Figure 3:
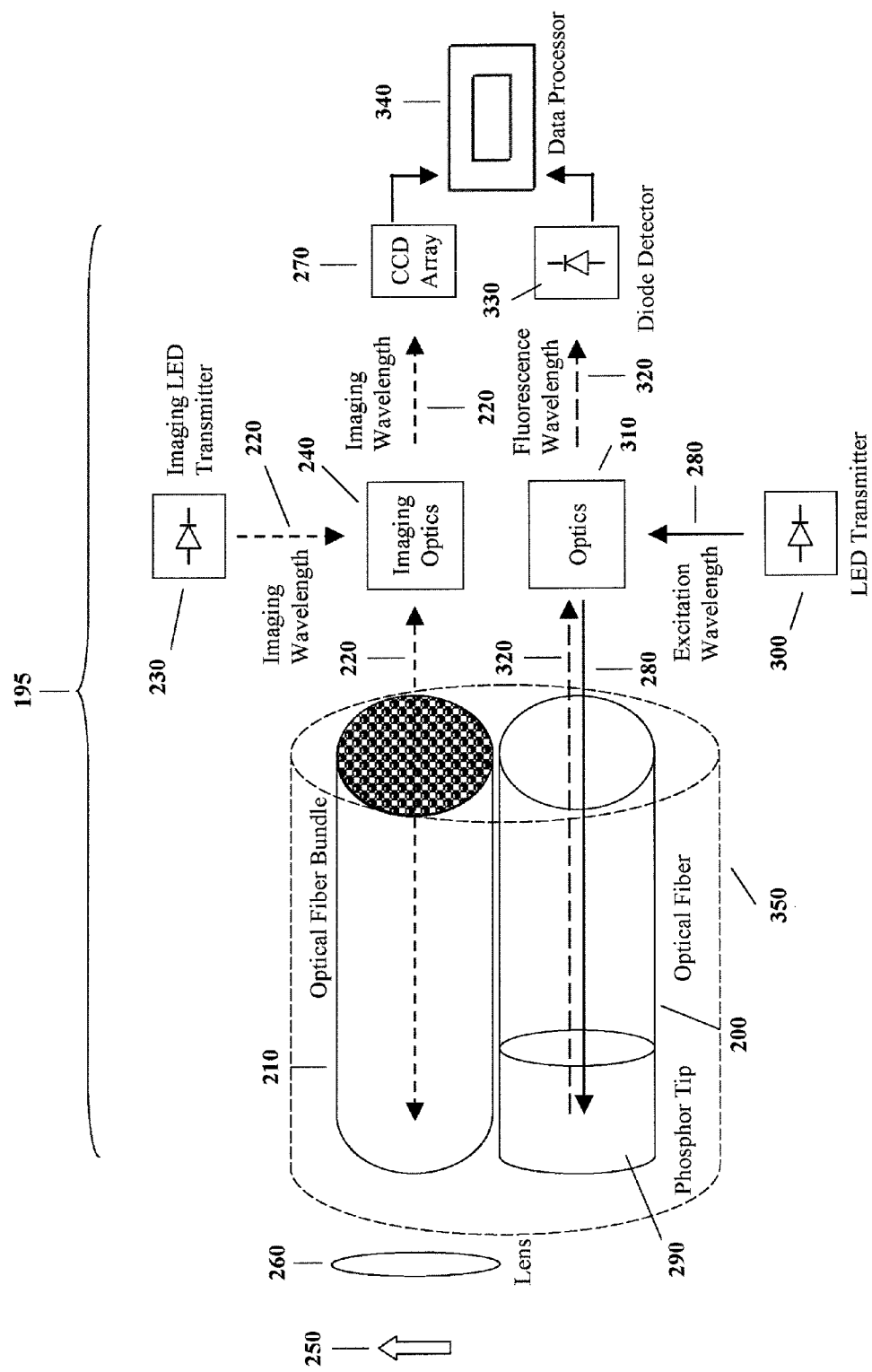
FIG. 3 is a schematic block diagram illustration of a fiber-optic temperature sensor with a separate imaging fiber bundle.

In the embodiment illustrated schematically in FIG. 3, an imaging temperature sensor 195 includes a temperature-sensing optical fiber 200 and an imaging optical fiber bundle 210 arranged and fixed, for example, but not limited to, substantially adjacent relative to each other. Electromagnetic radiation, such as, but not limited to, light 220 for imaging is generated from a source 230 such as, but not limited to, a light emitting diode (LED) and directed to the optical fiber bundle 210 by imaging optics 240 such as, but not limited to, beamsplitters, gratings, or waveguide directional couplers, propagates through the optical fiber bundle 210, and encounters an object 250 via a lens 260. The light 220 is reflected from the object 250 and through the lens 260 back to the optical fiber bundle 210. The light 220 returning through the optical fiber bundle 210 is separated by the imaging optics 240 and directed to a detector 270 such as, but not limited to, a CCD array or a camera, where it may be digitized.

Excitation electromagnetic radiation such as, but not limited to, light 280 for a phosphor or temperature-sensing component 290 located at an end of the temperature-sensing optical fiber 200 is generated by, but not limited to, a light source 300 such as, but not limited to, a LED and directed by optics 310 such as, but not limited to, beamsplitters, gratings, or waveguide directional couplers, through the temperature-sensing optical fiber 200. Fluorescent light 320 from the phosphor tip 290 propagates through the temperature-sensing optical fiber 200 and is subsequently directed by the optics 310 to a detector 330 such as, but not limited to, a diode detector.

Temporal decay characteristics (such as a time constant for the temporal decay) may be measured by a data processor 340, which may also be used for image processing the output of the camera 270. An outer frame or housing 350, which may be flexible, can be, but is not required to be, used to contain the two optical fibers.

Figure 4:
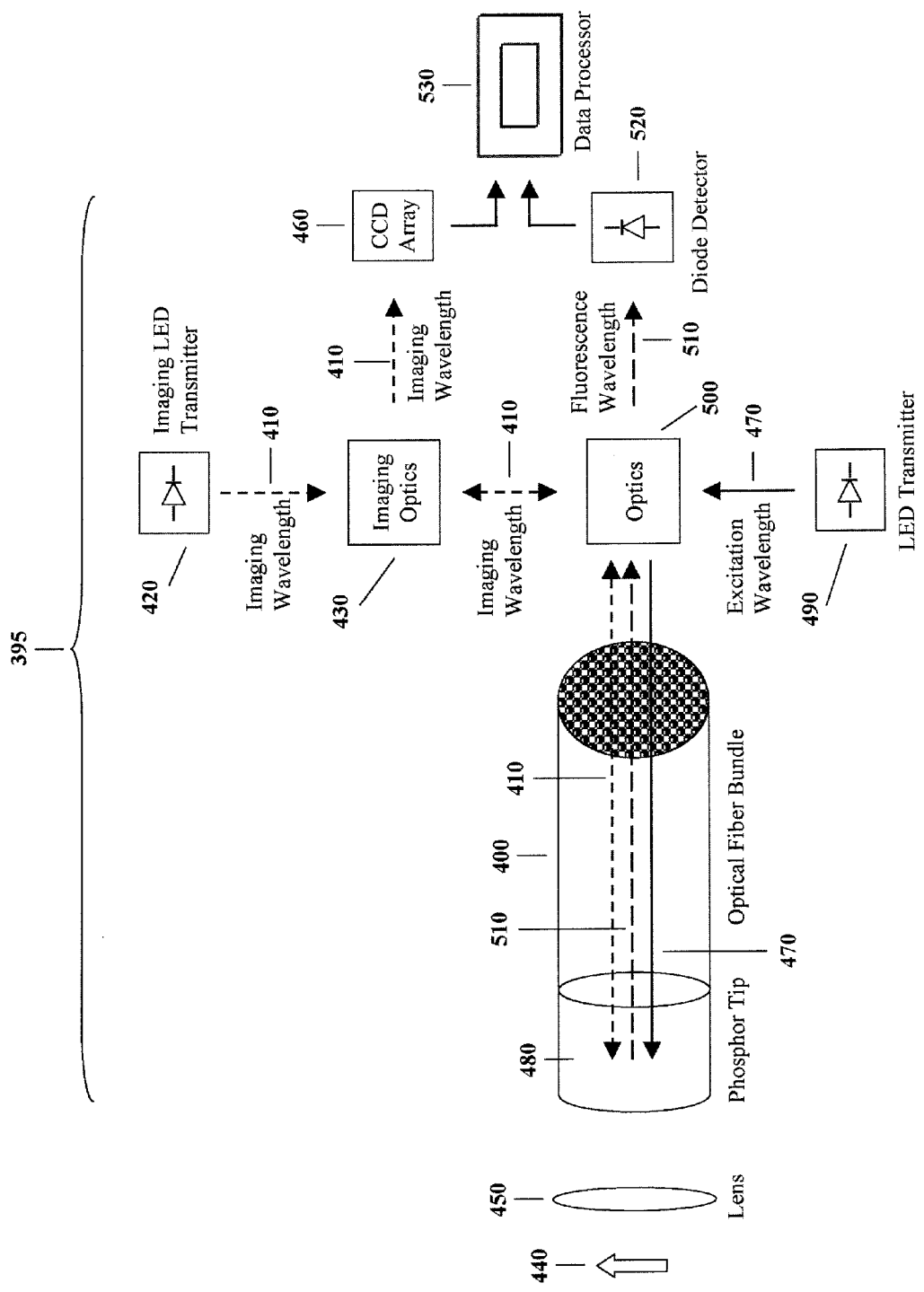
FIG. 4 is a schematic block diagram illustration of a fiber-optic temperature sensor with a shared imaging fiber bundle.

Another embodiment of an imaging temperature sensor 395 is presented in FIG. 4, in which the temperature sensing and imaging functions are both provided via an optical fiber bundle 400. Electromagnetic radiation such as, but not limited to, light 410 for imaging is generated from a source 420 such as, but not limited to, a light emitting diode (LED) and directed to the optical fiber bundle 400 by imaging optics 430 such as, but not limited to, beamsplitters, gratings, or waveguide directional couplers, propagates through the optical fiber bundle 400, and encounters an object 440 via a lens 450. The light 410 is reflected from the object 440 and through the lens 450 back to the optical fiber bundle 400. The light 410 returning through the optical fiber bundle 400 is separated by the imaging optics 430 and directed to a camera 460 such as, but not limited to, a CCD array, where it may be digitized.

Excitation electromagnetic radiation such as, but not limited to, light 470 for a phosphor or temperature-sensing component 480 located at an end of the optical fiber bundle 400 is generated by a light source 490 such as, but not limited to, a LED and directed by optics 500 such as, but not limited to, beamsplitters, gratings, or waveguide directional couplers, through the optical fiber bundle 400. Fluorescent light 510 from the phosphor tip 480 propagates through the optical fiber bundle 400 and is subsequently directed by the optics 500 to a detector 520 such as, but not limited to, a diode detector. Some or all of the fibers comprising the optical fiber bundle 400 may propagate a portion or substantially all of, one, or both, of the light 410 and the light 470.

Temporal decay characteristics (such as a time constant for the temporal decay) may be measured by a data processor 530, which may also be used for image processing the output of the detector in the form of, but not limited to, camera or CCD array 460.

Thus, an imaging temperature sensor may include, for example, but not limited to, a fiber optic bundle for imaging and one or more fiber optic cables for temperature sensing. Imaging wavelengths may be kept separate from temperature sensing wavelengths so that means can be used for keeping them separate and improving data quality for both functions.

One use of the imaging temperature sensing system may be in the form of a medical application, but is not limited thereto, monitoring temperatures at various locations within the body of a patient undergoing an endoscopic examination or treatment. The imaging temperature sensing system of FIG. 4, for example, could provide temperature information for the location being imaged within the body of the patient providing additional diagnostic data. In this embodiment, the imaging temperature sensing system could be in the general form of an endoscope that is manipulated by medical personnel to position one end of the device within the body of the patient.

Although the invention has been described with respect to various embodiments, it should be realized this invention is also capable of a wide variety of further and other embodiments within the spirit and scope of the appended claims.

What is claimed is:

1. An imaging temperature sensing system comprising:
   first means for propagating electromagnetic radiation at a first optical wavelength band and electromagnetic radiation at a second optical wavelength band;
   means for generating said electromagnetic radiation at said first optical wavelength band;
   means for absorbing said electromagnetic radiation at said first optical wavelength band and emitting said electromagnetic radiation at said second optical wavelength band;
   said electromagnetic radiation at said second optical wavelength band incorporating features therein dependent upon the temperature of said absorbing means;
   means for separating said electromagnetic radiation at said second optical wavelength band and said electromagnetic radiation at said first optical wavelength band;
   means for detecting said electromagnetic radiation at said second optical wavelength band and providing an output after passing through said first propagating means;
   means for receiving said output and processing said features dependent upon the temperature of said absorbing means to substantially determine said temperature;
   second means for propagating electromagnetic radiation at a third optical wavelength band transmitted to and received from an object;
   means for generating said electromagnetic radiation at said third optical wavelength band;
   means for substantially separating transmitted and received said electromagnetic radiation at said third optical wavelength band passing through said second propagating means;
   means for detecting said electromagnetic radiation at said third optical wavelength band after passing through said second propagating means;

means for processing said electromagnetic radiation at said third optical wavelength band received from said object in order to yield image data of said object.

2. The imaging temperature sensing system of claim 1 wherein:

said electromagnetic radiation comprises light.

3. The imaging temperature sensing system of claim 2 with means for imaging said object.

4. The imaging temperature sensing system of claim 1 wherein:

at least one of said propagating means comprises an optical fiber.

5. The imaging temperature sensing system of claim 1 wherein:

said first propagating means and said second propagating means are contained within a common structure.

6. An imaging temperature sensing system comprising:

means for propagating electromagnetic radiation at a first optical wavelength band and electromagnetic radiation at a second optical wavelength band, as well as propagating electromagnetic radiation at a third optical wavelength band transmitted to and received from an object;

means for generating said electromagnetic radiation at said first optical wavelength band;

means for absorbing said electromagnetic radiation at said first optical wavelength band and emitting said electromagnetic radiation at said second optical wavelength band;

said electromagnetic radiation at said second optical wavelength band incorporating features therein dependent upon the temperature of said absorbing means;

means for generating said electromagnetic radiation at said third optical wavelength band;

means for combining said electromagnetic radiation at said first optical wavelength band and, said electromagnetic radiation at said third optical wavelength band and separating said electromagnetic radiation at said second optical wavelength band and said third optical wavelength band;

means for detecting said electromagnetic radiation at said second optical wavelength band and providing a first output after passing through said propagating means;

means for receiving said first output and processing said features dependent upon the temperature of said absorbing means to substantially determine said temperature at substantially said absorbing means;

means for detecting said electromagnetic radiation at said third optical wavelength band after passing through said propagating means, and providing a second output; and means for receiving said second output and processing said electromagnetic radiation at said third optical wavelength band received from said object yielding image data of said object.

7. The imaging temperature sensing system of claim 6 wherein:

said electromagnetic radiation comprises light.

8. The imaging temperature sensing system of claim 7 with means for imaging said object.

9. The imaging temperature sensing system of claim 6 wherein:

at least one of said propagating means comprises an optical fiber.

\* \* \* \* \*